(12) United States Patent
Ramos-Pereira

(10) Patent No.: US 8,435,255 B2
(45) Date of Patent: May 7, 2013

(54) SURGICAL CLAMP

(76) Inventor: Raúl León Ramos-Pereira, San Juan, PR (US)

( * ) Notice: Subject to any disclaimer, the term of this patent is extended or adjusted under 35 U.S.C. 154(b) by 1051 days.

(21) Appl. No.: 12/427,444

(22) Filed: Apr. 21, 2009

(65) Prior Publication Data

US 2010/0268269 A1 Oct. 21, 2010

(51) Int. Cl.
*A61B 17/04* (2006.01)
*A61B 17/00* (2006.01)
*B25B 7/02* (2006.01)

(52) U.S. Cl.
USPC .............................. 606/148; 606/207; 81/418

(58) Field of Classification Search ................... 606/51, 606/52, 148, 205, 207; 600/104, 141, 142; 81/119, 176.3, 418
See application file for complete search history.

(56) References Cited

U.S. PATENT DOCUMENTS

| | | | | |
|---|---|---|---|---|
| 1,664,112 A | * | 3/1928 | Junemann | 606/158 |
| 3,364,933 A | * | 1/1968 | Leopold | 606/207 |
| 4,827,929 A | * | 5/1989 | Hodge | 606/139 |

* cited by examiner

*Primary Examiner* — Gary Jackson
*Assistant Examiner* — Michael Mendoza
(74) *Attorney, Agent, or Firm* — Eugenio J. Torres-Oyola

(57) ABSTRACT

An apparatus and method an apparatus and method for suturing, wherein said apparatus is a surgical instrument comprising a pair a cross members having securing means for pivotally securing the cross members to one another creating a first end, wherein the cross members second end comprises a locking device for locking the cross member and the first end comprises a clamping surface at a distal ends having at least two opposed curves forming a S-shaped sections having a outer smooth surface and a serrated inner surface assisting the suture process avoiding proximal slippage of suture material while tying a clamped structure.

9 Claims, 5 Drawing Sheets

SURGICAL CLAMP

STATEMENT REGARDING FEDERALLY SPONSORED RESEARCH AND DEVELOPMENT

N/A

RELATED APPLICATIONS

N/A

BACKGROUND OF THE INVENTION

1. Field of the Invention

The invention is related to an apparatus and method for suturing, more particularly to surgical instrument and the use of said surgical instrument for suture during surgical operations which avoids the proximal slippage of suture material while tying a clamp structure.

2. Discussion of the Background

Surgical clamps, such as hemostatic clamp is a surgical tool which resembles a set of scissors with a locking clamp. A set of hemostats comes in several different sizes and types, for example, Kelly, Crile, and Halstead; and any given surgery may require the use of a number of hemostats. Commonly is used in both surgery to control bleeding, especially from a torn blood vessel, until the bleeding can be repaired by stitches, suture or other surgical techniques.

Currently several surgical instruments and/or clamping instruments including hermostatic clamps, as mentioned before, are provided with angled distal end with respect to first portion, for example acute angle or right angle at the distal end with respect to the handle, as shown in FIG. 1 and FIG. 2, in order to easily access certain body part. However none of the current forceps, tongs, clamps or pliers is provided with a distal end that not just access and holds certain body part but also assists efficiently the suture process of a blood vessel.

For example U.S. Pat. No. 4,226,240 to Walter Jr. discloses a surgical forceps comprising the gripping arms and terminating with a pair of slightly curved mating jaws having aligned notches disposed on their outer surfaces to accommodate a needle for sutures. The pair of mated jaws are disposed in a plane substantially perpendicular to the plane containing the pair of end members. Walter invention's distal end or extremity segment terminates with slightly curved or arcuate mating jaws having notches to accommodate a needle for suture. Even when the structure is provided with a portion or notches to accommodate a needle the distal end does not assist the suture process efficiently.

Another example is U.S. Pat. No. 2,887,111 to Leyro which discloses a surgical forceps that simplifies the movement of the operative process by not requiring, apart from the pincer, any other instrument apart from the cutting scissors and catgut or thread employed in the tieing of veins. Leyro's invention seems to shorten the surgical time but the need of an additional instrument is not convenient in several surgical procedures.

Further U.S. Pat. No. 3,364,933 to Bogni discloses a surgical clamp including a distal end with an obtuse angle provided with smooth surface. Even when the obtuse angle smooth surface might help with the suture process it does not assist the suture process efficiently since no holding feature for the suture material is provided.

All the clamping instruments currently known, including the ones mentioned above, fails to provide a surgical instrument that not just provides a clamping action and angled distal end but also assists the suture process efficiently.

SUMMARY OF THE INVENTION

The present invention provides an apparatus and method for suturing, wherein said apparatus is a surgical instrument comprising a pair a cross members having securing means for pivotally securing the cross members to one another creating a first end, wherein the cross members second end comprises a locking device for locking the cross member and the first end comprises a clamping surface at a distal ends having at least two opposed curves forming a S-shaped sections having a outer smooth surface and a serrated inner surface assisting the suture process in such way that overcomes the disadvantages of the Prior Art.

Another object of the invention is to provide a method for suturing during operation without the need of several instruments.

Another object of the invention is to provide a surgical instrument that avoids proximal slippage of suture material while tying a clamped structure.

Yet another object of the present invention is to provide a surgical instrument with grasping structure.

The invention itself, both as to its configuration and its mode of operation will be best understood, and additional objects and advantages thereof will become apparent, by the following detailed description of a preferred embodiment taken in conjunction with the accompanying drawing.

The Applicant hereby asserts, that the disclosure of the present application may include more than one invention, and, in the event that there is more than one invention, that these inventions may be patentable and non-obvious one with respect to the other.

Further, the purpose of the accompanying abstract is to enable the U.S. Patent and Trademark Office and the public generally, and especially the scientists, engineers, and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

BRIEF DESCRIPTION OF THE DRAWINGS

The accompanying drawings which are incorporated herein constitute part of the specifications and illustrate the preferred embodiment of the invention.

DESCRIPTION OF THE PREFERRED EMBODIMENT

Figure 1:
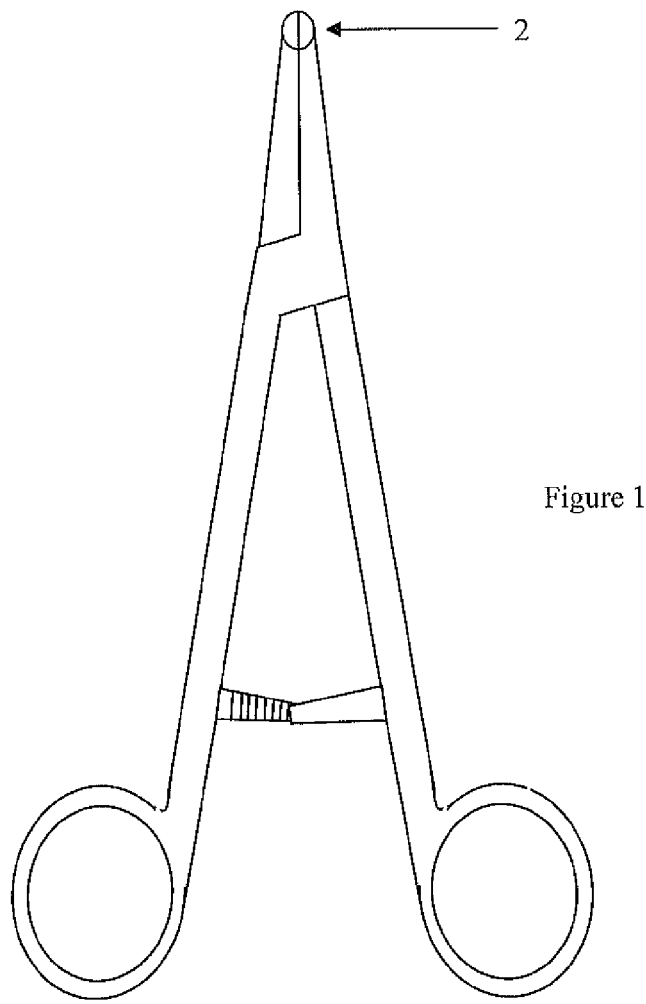
FIG. 1 is a top view of related art.
Figure 2:
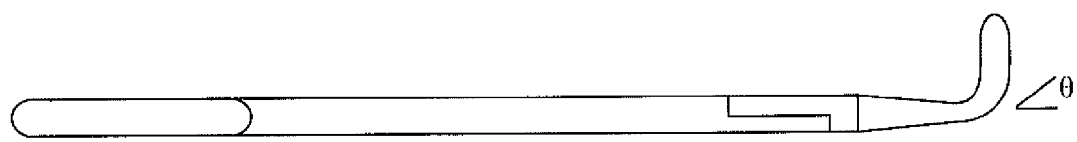
FIG. 2 is a side view of related art.
Figure 3:
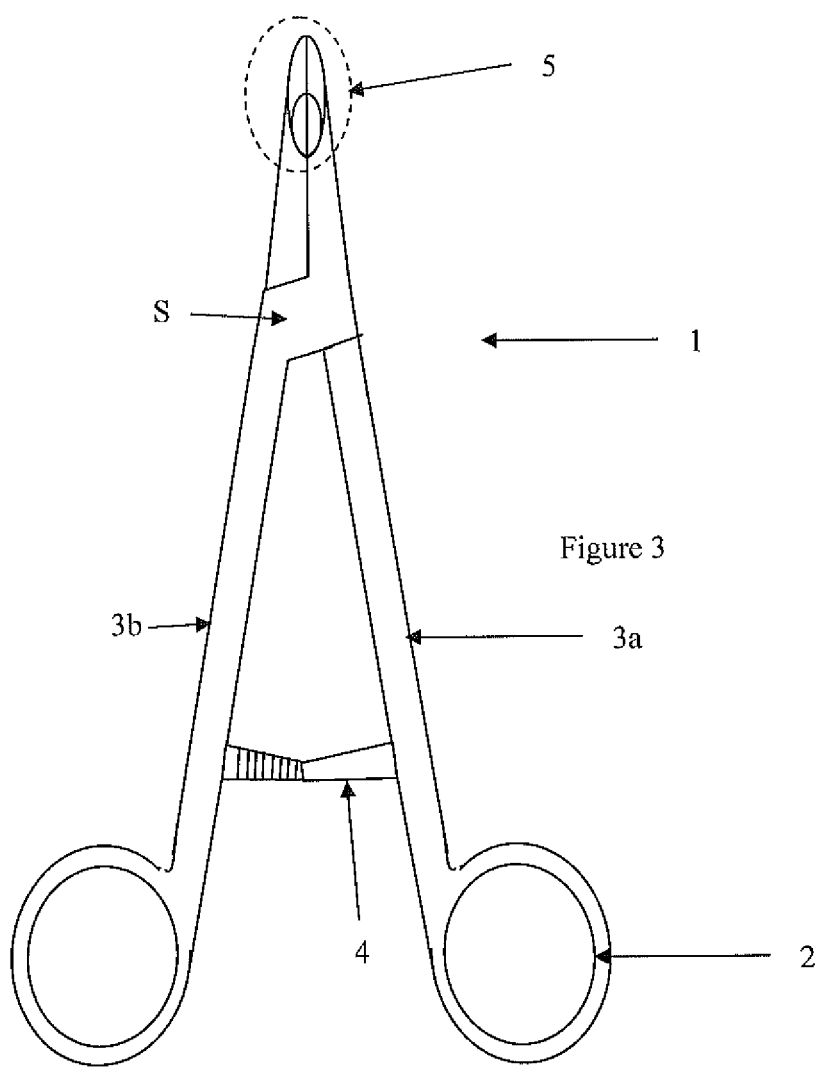
FIG. 3 is a top view of the present invention.

The present invention, as shown in FIG. 3, discloses a surgical instrument 1 comprising a pair a cross members 3a,3b having securing means S for pivotally securing the cross members 3a,3b to one another dividing the surgical instrument 1 in a first end 5 and second end 3, wherein the second end 3 comprises a locking device 4 for locking the cross member 3a,3b and is terminated by finger receiving rings 2; and the first end 5 comprises a clamping surface at a distal end.

Figure 4:
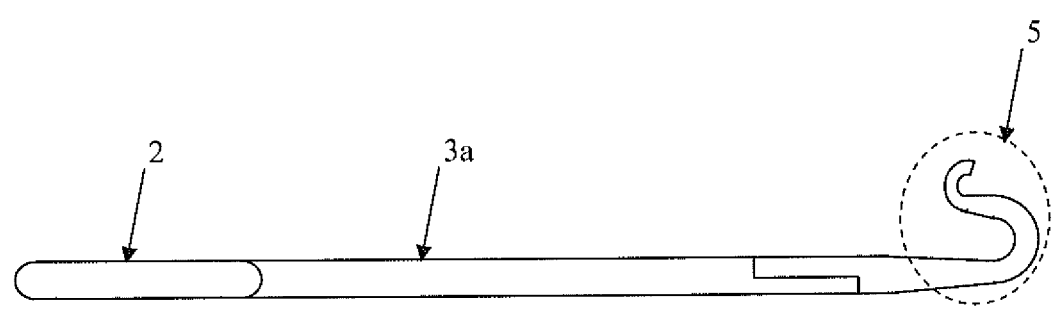
FIG. 4 is a side view of the present invention.
Figure 5:
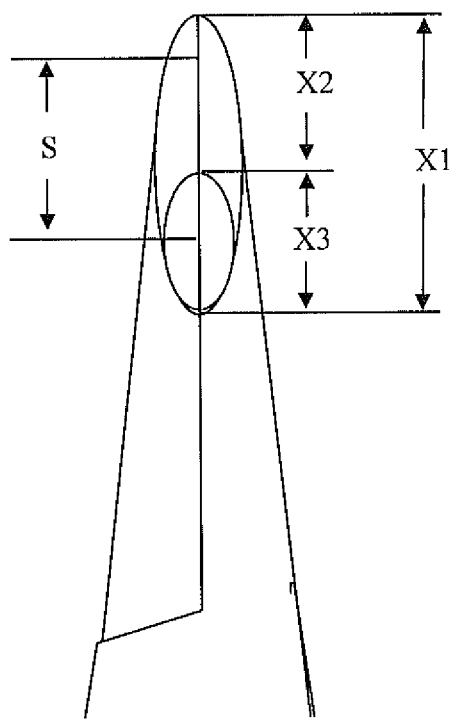
FIG. 5 is an exploded top view of present invention scissors ends.

The first end 5 clamping surface extends perpendicular to the surgical instrument 1 main body, as shown in FIG. 4, forming an S-shaped distal end. The S-shaped distal end comprises two opposed curves, one on top of the other, wherein the first curve 5a is dimensionally bigger than the second curve. The dimensions of the curves, as show in FIG. 5, may vary depending on the use, for example in order to reach a body part the first curve's length X1 may be extended. However the second curve's length X3 is smaller than the first curve's length X1 at all time. The preferred invention discloses distance difference X2 between the first curve's length X1 and the second curve's length X3, said distance X2 is larger than the second curve's length X3. It is important to understand that the second curve 5b is formed to provide a recess R which main purpose is to hold the suture material 7 in position avoiding the displacement of the suture material 7 in the direction opposed to the clamped structure. The dimensions of said second curve 5b affect the area cover by the surgical instrument 1, therefore the smaller the curve or recess R the easier is to handle the surgical instrument 1 during the surgical procedure. The recess is not intended to be in contact with the clamped surface because this will avoids the access of the suture material 7 to said recess R.

Figure 6:
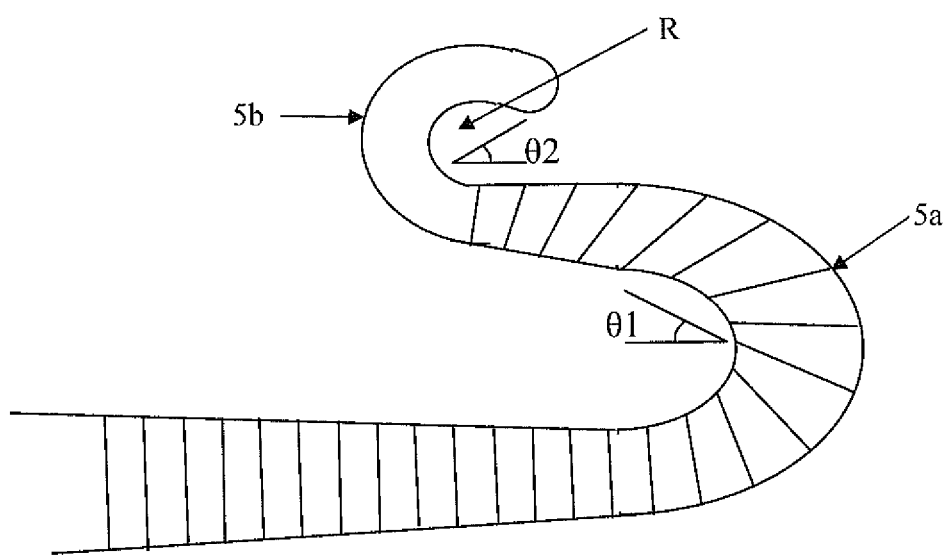
FIG. 6 is an exploded side view of present invention scissors ends.
Figure 7:
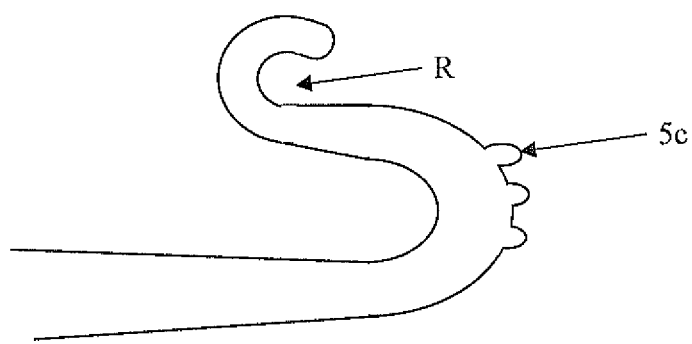
FIG. 7 is an exploded side view of present invention scissors ends holding teeth.
Figure 8:
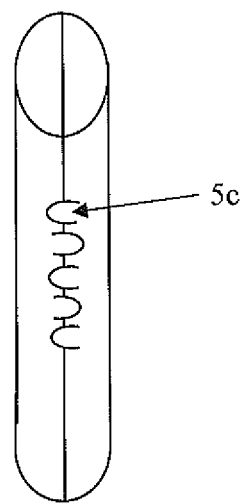
FIG. 8 is an exploded top view of present invention scissors ends with holding teeth.
Figure 9A:
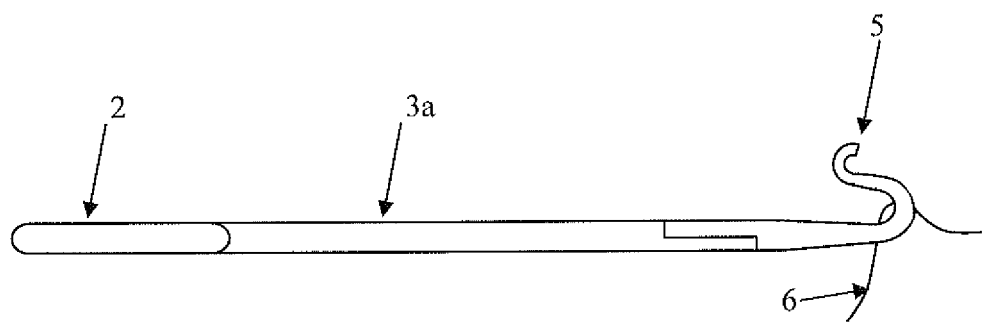
FIG. 9a-9d shows the slippage process of the suture material while trying using the present invention.
Figure 9B:
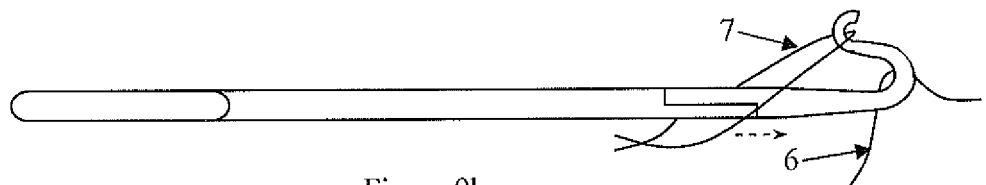
Figure 9C:
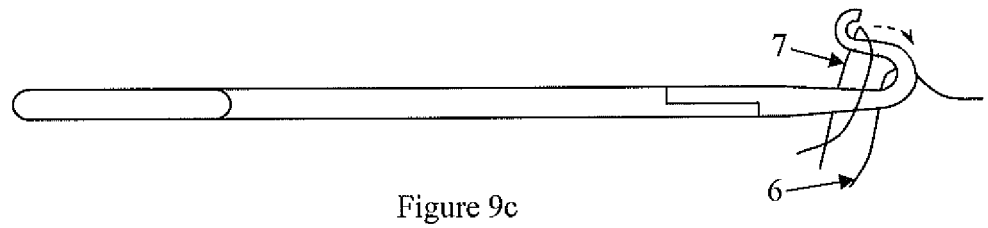
Figure 9D:
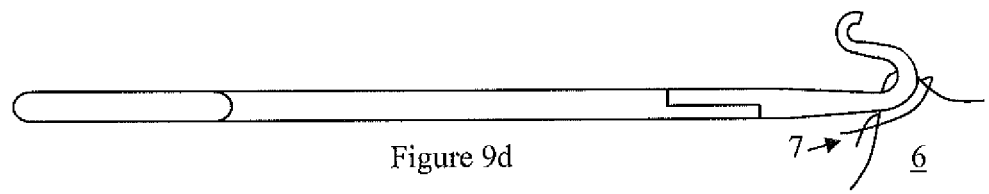

FIG. 6, discloses the inner surface of the clamping surface wherein said inner surface is serrated, either longitudinally or transversely. Further each curve 5a,5b is angled for several reasons. The first curve 5a is angled, more particularly at the segment of the first curve 5a that connect with the second curve 5b, in order to provide a slope between the curves in such way that the suture material travels over the inclined smooth surface S from the distal end or recess R toward the clamped structure. The first angle θ1 for the first curve 5a is preferred to be equal to or greater than 60 degrees. The second curve 5b or recess R which main purpose is to avoids the slippage of the suture material 7 in the direction opposed to the clamped structure has an preferable second angle θ2, more particularly to the second curve part that avoids the suture material displacement in the direction opposed to the clamped structure which is relative smaller than the first angle θ1. It is important to understand that the segment connecting the first 5a and second curve 5b extends Further, as shown in FIG. 7 and FIG. 8, the first curve which is the curve that contact the clamped structure includes a griping structure comprising several protrusion or tooth 5c extended from the first curve 5a surface.

FIG. 9 show several steps of the suturing process. The surgical instrument, as mentioned above, is provided with locking means that are intended to lock the first's cross member ends while said cross member are clamping a structure 6. The clamped structure, usually a blood vessel, is in close contact with the distal end 5, as shown in FIG. 9a. It is important to point out that the first curve 5a is the portion in full contact with the clamped structure 6. The second curve 5b is not contacting the clamped structure 6 because it will complicate the placement of the suture material at said second curve 5b recess R. After clamping the structure 6, the suture material 7 is positioned at the second curve 5b is such way that the recess R hold said suture material facing the front part of the surgical instrument 1 while the user pulls the suture material 7 toward the finger receiving rings 2. The suture material 7 is crossed, in order to make a knot, around and at the back part of the surgical instrument 1 away from the distal end 5. Further the suture material 7 is push toward the clamped structure 6, as shown in FIG. 9c. The inclined smooth surface S connecting the first curve 5a assists the slippage of the suture material 7 toward said clamped surface 6. FIG. 9d shows the final position of the suture material 7. The knot is tied and fixed in order to control the bleeding at the clamped structure 6. The surgical clamp 1 of the present invention avoids the proximal slippage of suture material while tying a clamped structure without the need of several instruments while assisting the suturing process.

While the invention has been described as having a preferred design, it is understood that many changes, modifications, variations and other uses and applications of the subject invention will, however, become apparent to those skilled in the art without materially departing from the novel teachings and advantages of this invention after considering this specification together with the accompanying drawings. Accordingly, all such changes, modifications, variations and other uses and applications which do not depart from the spirit and scope of the invention are deemed to be covered by this invention as defined in the following claims and their legal equivalents. In the claims, means-plus-function clauses, if any, are intended to cover the structures described herein as performing the recited function and not only structural equivalents but also equivalent structures.

All of the patents, patent applications, and publications recited herein, and in the Declaration attached hereto, if any, are hereby incorporated by reference as if set forth in their entirety herein. All, or substantially all, the components disclosed in such patents may be used in the embodiments of the present invention, as well as equivalents thereof. The details in the patents, patent applications, and publications incorporated by reference herein may be considered to be incorporable at applicant's option, into the claims during prosecution as further limitations in the claims to patentable distinguish any amended claims from any applied prior art.

The invention claimed is:

1. A surgical clamp instrument comprising;
    a pair a cross members having securing means for pivotally securing the cross members to one another creating a first end and a second end,
    wherein the cross members second end comprises a locking device for locking said pair cross member is a steady position and finger receiving rings,
    wherein the cross members first end comprises a clamping surface at a distal end having at least a first curve, second curve and an inclined surface, wherein said first curve and second curves opposed each other and the first curve's dimensions are larger than said second curve's dimensions, and wherein said second curve is positioned on top of said first curve comprising a recess, wherein said first curve and second curve formed an S-shaped section at the distal end.

2. A surgical clamp instrument as in claim 1 wherein said first curve and second curve comprises a serrated inner surface and a smooth outer surface assisting slippage of a suturing material.

3. A surgical clamp instrument as in claim 1 wherein said inclined surface and said first curve outer surface are slanted to assist the slippage of a suturing material.

4. A surgical clamp instrument as in claim 1 wherein said first curve comprises tooth extended from the first curve surface.

5. A surgical clamp instrument as in claim 1 wherein said first curve is angled to be equal to or greater than 60 degrees.

6. A surgical clamp instrument as in claim 1 wherein said first curve and second curve are angled and said second curve angle is smaller than the first curve angle.

7. A method for suturing comprising:
- a surgical clamp,
- a suture material,
- wherein said surgical clamp comprises pair a cross members having securing means for pivotally securing the cross members to one another creating a first end and a second end,
- wherein the second end comprises a locking device for locking said pair cross member is a steady position and finger receiving rings,
- wherein first end comprises a clamping surface at a distal ends having at least a first curve, second curve and an inclined surface, wherein said first curve and second curves opposed each other, wherein said second curve is positioned on top of said first curve comprising a recess,
- wherein a suturing process comprises;
- said surgical clamp first end clamping a structure at said distal end,
- placing said suture material at said recess while pulling said suture material toward said finger receiving rings,
- moving the suture material around the surgical instrument and away from the distal end,
- creating a compact intersection of interlaced suture material at the back part of said surgical instrument, pushing the suture material toward the clamped structure wherein said first curve surface assists the displacement of the suture material,
- tying the intersection of interlaced suture material to control the bleeding at the clamped structure; and releasing the clamped structure.

8. A method for suturing as in claim 7, wherein said first curve is in close contact of the clamped structure without blocking said recess.

9. A surgical clamp instrument comprising;
- a pair a cross members having securing means for pivotally securing the cross members to one another creating a first end and a second end,
- wherein the cross members second end comprises a locking device for locking said pair cross member in a steady position and finger receiving rings,
- wherein the cross members first end comprises a clamping surface at a distal end comprises at least a first curve and an inclined surface, wherein said inclined surface comprises a recess positioned on top of said first curve, wherein said first curve comprises a first concave configuration and said recess comprises a second concave configuration opposing each other and the first curve's dimensions are larger than said recess's dimensions.

* * * * *